US012797197B2

(12) United States Patent
El-Chafei et al.

(10) Patent No.: US 12,797,197 B2
(45) Date of Patent: Nov. 17, 2026

(54) ADDITIVELY MANUFACTURED ORTHOPAEDIC IMPLANTS AND MAKING THE SAME

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Mouhsin Ahmed El-Chafei, Arlington, TN (US); David W. Rister, Nesbit, MS (US); Jason Sells, Marion, TN (US); Dongyu Zang, Collierville, TN (US)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 569 days.

(21) Appl. No.: 18/272,204

(22) PCT Filed: Jan. 12, 2022

(86) PCT No.: PCT/US2022/012069
§ 371 (c)(1),
(2) Date: Jul. 13, 2023

(87) PCT Pub. No.: WO2022/155164
PCT Pub. Date: Jul. 21, 2022

(65) Prior Publication Data

US 2024/0065846 A1 Feb. 29, 2024

Related U.S. Application Data

(60) Provisional application No. 63/137,377, filed on Jan. 14, 2021.

(51) Int. Cl.
*A61F 2/36* (2006.01)
*A61F 2/30* (2006.01)

(52) U.S. Cl.
CPC ... *A61F 2/3603* (2013.01); *A61F 2002/30011* (2013.01); *A61F 2002/30784* (2013.01);
(Continued)

(58) Field of Classification Search
None
See application file for complete search history.

(56) References Cited

U.S. PATENT DOCUMENTS 7,879,106 B2 2/2011 McMinn
9,056,021 B2 6/2015 Turner
(Continued)

FOREIGN PATENT DOCUMENTS

EP 2774580 A1 9/2014
EP 3257475 A1 12/2017

OTHER PUBLICATIONS

International Search Report and Written Opinion for the International Application No. PCT/US2022/012069, mailed Apr. 26, 2022, 11 pages.

*Primary Examiner* — Anthony M Liang
(74) *Attorney, Agent, or Firm* — KDW Firm PLLC

(57) ABSTRACT

The present disclosure provides an additively manufactured resurfacing implant (100) configured for use in a resurfacing surgery in which one or more porous regions (130) are provided at an internal fixation surface of a resurfacing head (110) of the resurfacing implant. In various embodiments, the additively manufactured resurfacing implant comprises one or more substantially nonporous regions that correspond to the resurfacing head and a stem (120) of the resurfacing implant and one or more porous regions that are positioned on an internal surface of the resurfacing head. The present
(Continued)

disclosure also provides an intermediate constructions and an additive manufacturing process for forming such a resurfacing implant.

14 Claims, 4 Drawing Sheets

(52) U.S. Cl.
CPC ............... *A61F 2002/30968* (2013.01); *A61F 2002/3097* (2013.01); *A61F 2002/30985* (2013.01); *A61F 2310/00023* (2013.01); *A61F 2310/00029* (2013.01); *A61F 2310/00089* (2013.01)

(56) References Cited

U.S. PATENT DOCUMENTS

| | | | |
|---|---|---|---|
| 9,974,657 | B2 | 5/2018 | McMinn |
| 2012/0029650 | A1 | 2/2012 | Bruce |
| 2014/0172111 | A1 | 6/2014 | Lang |
| 2014/0257507 | A1 | 9/2014 | Wang et al. |
| 2017/0027624 | A1 | 2/2017 | Wilson |
| 2017/0296699 | A1 | 10/2017 | Khowaylo |

ADDITIVELY MANUFACTURED ORTHOPAEDIC IMPLANTS AND MAKING THE SAME

CROSS-REFERENCE TO RELATED APPLICATIONS

This application is a National Phase filing of International Application No. PCT/US2022/012069, filed Jan. 12, 2022, which application claims the benefit of the filing date of U.S. provisional patent application No. 63/137,377, filed Jan. 14, 2021, entitled "ADDITIVELY MANUFACTURED ORTHOPAEDIC IMPLANTS AND MAKING THE SAME" the entirety of each application is incorporated by reference herein.

FIELD OF THE DISCLOSURE

The present disclosure is directed to orthopedic implants, and more particularly to additively manufactured orthopedic implants and additive manufacturing methods for forming orthopedic implants.

BACKGROUND

Traditional total hip replacements involve inserting a stem of a femoral implant into a medullary canal of a patient's femur after the femur has been resected at the distal end of the femoral neck. The stem is usually tapered such that its sides gradually converge from a wider proximal end to a narrower distal end. This configuration allows the stem to fill the majority of the medullary canal as the femur gradually narrows in a distal direction and this helps to anchor the implant in the femur. A rounded tip is provided at the distal end of the stem and a femoral neck and a head is provided at the proximal end. The head is typically in the form of a spherical ball that is configured for location within a corresponding acetabular cup.

In recent years, more conservative approaches such as hip resurfacing methods, including Birmingham Hip Resurfacing (BHR) methods, have been employed as an alternative to total hip replacement. In this case, the aim is to save as much healthy bone as possible, and the femur is preferably resected towards the proximal end of the femoral neck or through the lower portion of the femoral head. An example of one such femoral head resurfacing implant 100 is shown schematically in FIG. 1. The resurfacing implant 100 includes a resurfacing head 110 having a proximal end 110*p*, a distal end 110*d*, an internal fixation surface 116, shaped to locate the head 110 on the remaining bone of the femur, and a partially spherical external articulating surface 112, which is configured for location within a corresponding acetabular cup. The internal fixation surface 116 and the external articulating surface 112 meet at a rim 114. The resurfacing implant 100 shown also has a stem 120, which projects from the center of the internal surface of the head 110.

Strength, fixation, and wear resistance are important characteristics of resurfacing heads. A polished resurfacing head limits wear between the head and liner construct, and strength and wear characteristics are correlated with proper selection of materials. Traditionally, hip resurfacing heads have been formed from solid alloys such as cobalt chromium alloys and have not included a porous coating.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

The present disclosure provides an additively manufactured resurfacing implant configured for use in a resurfacing surgery in which one or more porous regions are provided at an internal fixation surface of a resurfacing head of the resurfacing implant.

In various embodiments, the additively manufactured resurfacing implant comprises one or more substantially nonporous regions (defined herein as having a porosity ranging from 0% porosity up to a maximum porosity of at most 2%, typically ranging from 0% to 1% porosity) and one or more adjacent porous regions (defined herein as having a porosity of at least 40%, typically a porosity ranging from 46% to 80% porosity).

In various embodiments, the additively manufactured resurfacing implant comprises one or more substantially nonporous regions that correspond to a resurfacing head and a stem of the resurfacing implant and one or more porous regions that are positioned on an internal surface of the resurfacing head.

In various embodiments, the one or more porous regions may range from 100 to 6000 microns in thickness.

In various embodiments, the one or more porous regions may become progressively thinner as one approaches a distal end of the resurfacing head.

The present disclosure also provides an additively manufactured intermediate construction having one or more external or internal support structures, which support structures are subsequently removed in whole or in part to form a resurfacing implant configured for use in a resurfacing surgery in which one or more porous regions are provided at an internal fixation surface of a resurfacing head of the resurfacing implant. In various embodiments, the additively manufactured intermediate construction comprises one or more substantially nonporous regions and one or more adjacent porous regions.

In various embodiments, an additively manufactured intermediate construction is provided which comprises (a) one or more substantially nonporous regions that correspond to a resurfacing head, a stem and an external support structure in the form of a capping structure and (b) one or more porous regions that are positioned on an internal surface of the resurfacing head. In these embodiments, the capping structure acts to stabilize the intermediate construction during the manufacturing process, after which the capping structure is removed by a suitable process to form a resurfacing implant. In some of these embodiments, the capping structure may be in the form of a plate and/or may contain one or more apertures.

In various embodiments, an additively manufactured intermediate construction is provided which comprises (a) one or more substantially nonporous regions that correspond to a resurfacing head, a plurality internal support structures in the form of gussets which extend inward into a central portion of the resurfacing head from an internal surface of the resurfacing head, a stem, and, optionally, a capping structure and (b) porous regions that are positioned on internal surfaces of the resurfacing head between the gussets. In these embodiments, the substantially nonporous gussets and optional capping structure act to stabilize the intermediate construction during the manufacturing process, after which all or a portion of the substantially nonporous gussets and optional capping structure are removed by a suitable process to form a resurfacing implant.

In various embodiments, an additively manufactured intermediate construction is provided which comprises (a) one or more substantially nonporous regions that correspond to a resurfacing head, a stem, and, optionally, a capping structure and (b) one or more porous regions positioned on an internal surface of the resurfacing head that include a plurality of internal support structures in the form of porous gussets that extend inward into a central portion of the resurfacing head. In these embodiments, the porous gussets and optional capping structure act to stabilize the intermediate construction during the manufacturing process, after which all or a portion of the porous gussets and the optional capping structure are removed by a suitable process to form a resurfacing implant.

In various embodiments, the porous regions and the substantially nonporous regions of the additively manufactured resurfacing implants and the intermediate constructions of the present disclosure may be formed from metallic materials selected from groups consisting of zirconium, zirconium alloy, titanium, tantalum, hafnium, niobium and any combination thereof, or cobalt-chromium alloys and stainless steel, among others.

In various embodiments, the porous regions and the substantially nonporous regions of the additively manufactured resurfacing implants and the intermediate constructions of the present disclosure are made of the same metallic material.

In various embodiments the substantially nonporous regions, the porous regions, or both the substantially nonporous regions and the porous regions of the additively manufactured resurfacing implants and the intermediate constructions of the present disclosure may have an exterior layered or single-species ceramic surface layer ranging in thickness, for example, from 0.1 to 25 microns in thickness, overlaying a diffusion hardened zone with a minimum thickness of 2 microns, or a diffusion hardened exterior surface wherein the surface alloyed zone ranges in thickness, for example, from 5 to 100 microns.

The present disclosure also provides an additive manufacturing process for the formation of the resurfacing implants and the intermediate constructions described herein.

In some embodiments, resurfacing implants and the intermediate constructions may be produced in a layer-wise fashion by irradiating metallic powders that are dispensed one layer at a time, thereby converting the metallic powders into the substantially nonporous regions and the porous regions of the resurfacing implants and the intermediate constructions in a layer-by-layer fashion.

In some embodiments, the additive manufacturing process comprises repeatedly forming a layer of metallic powder and irradiating the layer of metallic powder with an energy source to melt, fuse and/or sinter the metallic powder until a resurfacing implant or an intermediate construction is formed that has one or more substantially nonporous regions and one or more substantially porous regions.

In various embodiments, the energy source is selected from a laser or electron beam.

In various embodiments, a laser beam or electron beam is scanned over a first layer of powder in a first direction, after which a second layer of metallic powder is provided over the first layer, and a laser beam or electron beam is scanned over the second layer of metallic powder in second direction that is transverse to the first direction.

In various embodiments, the metallic powders that are used in the additive manufacturing process are selected from zirconium alloy powders, titanium alloy powders and cobalt-chromium alloy powders, among others.

In various embodiments, the resurfacing implants and the intermediate constructions are subjected to a thermal treatment process.

In various embodiments, all or a portion of an internal support structure and/or an external support structure that is present in the intermediate construction is removed.

Embodiments of the present disclosure provide various advantages. As noted above, BHR heads have not traditionally included porous coatings. In the present disclosure, one or more porous regions are provided on the internal fixation surfaces of resurfacing heads in order to encourage bone/tissue in-growth. Because the rim of various known BHR heads is required to be particularly thin, the addition of a porous layer means that the thickness of the substantially nonporous portion of the head at the rim will be reduced, potentially reducing the strength of the implant. The present disclosure employs additive manufacturing methods to form resurfacing heads which have porous regions that cover all or a portion of the internal fixation surface the resurfacing heads. By applying either no porous region or only a very thin porous region at the rim, the impact associated with a reduction in substantially nonporous material thickness is minimized while at the same time bone/tissue in-growth is encouraged. The present disclosure also provides various internal and/or external support structures which are used to provide strength during formation of the resurfacing heads.

Further features and advantages of at least some of the embodiments of the present invention, as well as the structure and operation of various embodiments of the present invention, are described in detail below with reference to the accompanying drawings.

BRIEF DESCRIPTION OF THE DRAWINGS

By way of example, specific embodiments of the disclosed resurfacing implants and intermediate constructions will now be described, with reference to the accompanying drawings, in which.

Figure 1:
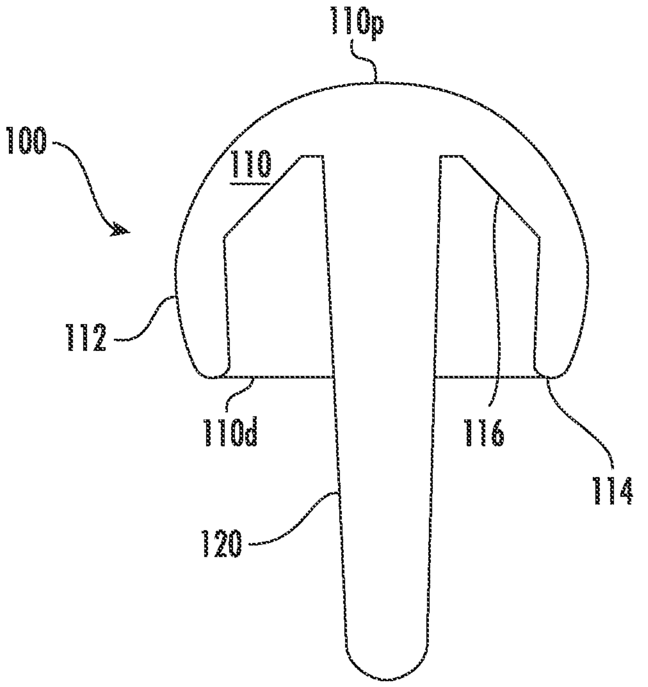
FIG. 1 PRIOR ART
FIG. 1 is a cross-sectional view of a resurfacing implant of the prior art.

The drawings are not necessarily to scale. The drawings are merely representations, not intended to portray specific parameters of the disclosure. The drawings are intended to depict example embodiments of the disclosure, and therefore are not considered as limiting in scope. In the drawings, like numbering represents like elements.

Furthermore, certain elements in some of the figures may be omitted, or illustrated not-to-scale, for illustrative clarity. The cross-sectional views may be in the form of "slices", or "near-sighted" cross-sectional views, omitting certain background lines otherwise visible in a "true" cross-sectional view, for illustrative clarity. Furthermore, for clarity, some reference numbers may be omitted in certain drawings.

DETAILED DESCRIPTION

Various features or the like of an additively manufactured resurfacing implant arranged and configured for use in a resurfacing surgery will now be described more fully hereinafter with reference to the accompanying drawings, in which one or more features of the resurfacing implant will be shown and described. Various features or the like of an additively manufactured intermediate construction arranged and configured for forming a resurfacing implant for use in a resurfacing surgery will also be described. Various features or the like of an additive method of forming a resurfacing implant or intermediate construction will further be described. It should be appreciated that the various features may be used independently of, or in combination, with each other. It will be appreciated that an additively manufactured resurfacing implant, additively manufactured intermediate construction and method as disclosed herein may be embodied in many different forms and should not be construed as being limited to the embodiments set forth herein. Rather, these embodiments are provided so that this disclosure will convey certain features of the resurfacing implant to those skilled in the art.

In various embodiments of the present disclosure, additively manufactured resurfacing implants and intermediate constructions are provided which comprise one or more substantially nonporous regions, which may, for example, promote strength and wear resistance of the implant, and one or more adjacent porous regions, which may, for example, promote bone or tissue growth into the implant.

The fact that the resurfacing implants and intermediate constructions of the present disclosure are additively manufactured means that the substantially nonporous regions and the porous regions of the same can have essentially any desired thickness. Typically, the substantially nonporous regions will constitute the bulk of the resurfacing implants or intermediate constructions, while the porous regions will range up to an average of roughly 1500 microns in thickness and will typically cover only a portion of the resurfacing implants or intermediate constructions. In some embodiments, the one or more porous regions may cover all or a portion of an internal surface of a resurfacing head. In those areas where one or more porous regions are present at the internal surface of the resurfacing head, the porous regions will typically range from 100 microns to 6000 microns in thickness. In the area near the rim of the resurfacing head, where it is desirable to maximize the thickness of the substantially nonporous material in order to maximize strength, the one or porous regions may either be absent or may be relatively thin (e.g., ranging from 0 to 100 microns in thickness). The fact that the one or more porous regions are additively manufactured at the same time as the substantially nonporous regions also means that porous regions can be formed that are tightly bound to the substantially nonporous regions and are of enhanced strength (e.g., for weight bearing purposes).

Figure 2:
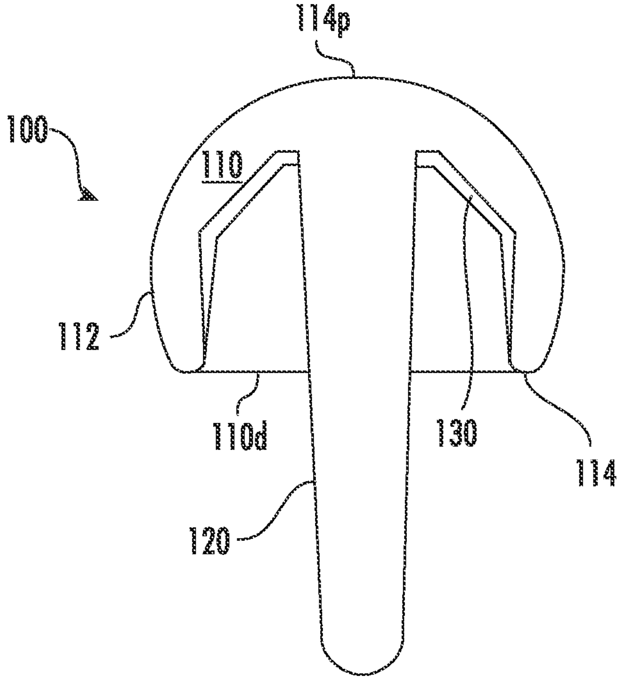
FIG. 2 is a cross-sectional view of an embodiment of a resurfacing implant in accordance with one or more features of the present disclosure.

Referring to FIG. 2, a resurfacing implant 100 is shown in which a porous region 130 is formed on an internal surface of the resurfacing head 110 to encourage bone/tissue ingrowth. The porous region 130 increases in thickness with increasing distance from rim 114 at the distal end 110*d* resurfacing head 110 in order to reduce the thickness of the substantially nonporous material forming the head 110 at the rim 114. The resurfacing implant 100 also includes a substantially nonporous stem 120, which projects from the center of the internal surface of the head 110.

Figure 3A:
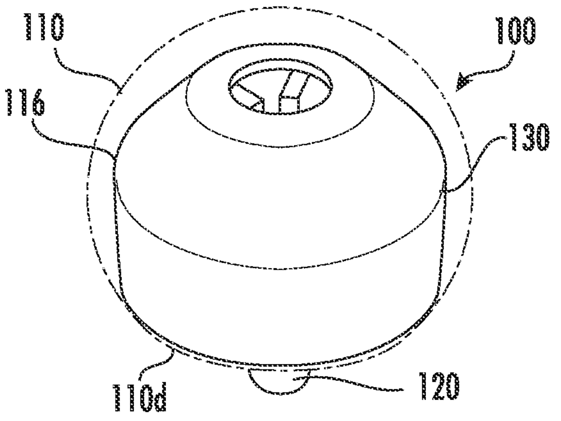
FIG. 3A is perspective view of an embodiment of an intermediate construction useful for forming a resurfacing implant in accordance with one or more features of the present disclosure.
Figure 3B:
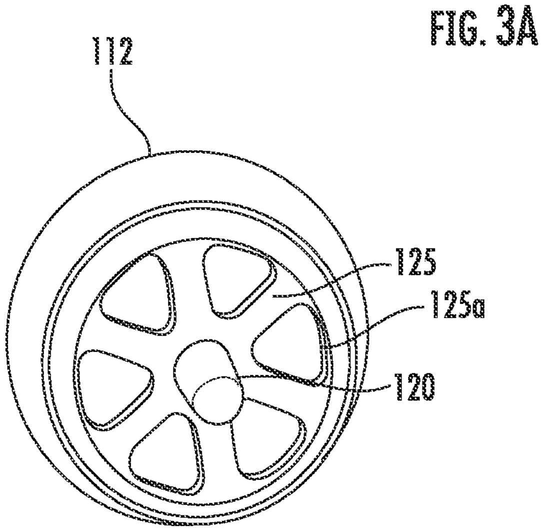
FIG. 3B is perspective view of substantially nonporous regions (e.g., resurfacing head, stem and cap) of the intermediate construction of FIG. 3A.
Figure 3C:
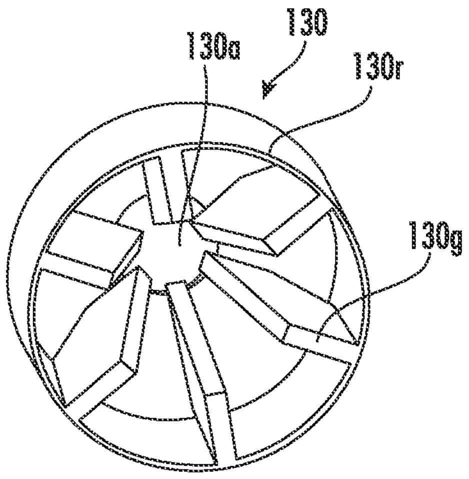
FIG. 3C is perspective view of a porous region of the intermediate construction of FIG. 3A.

FIG. 3A is partially transparent perspective view of an intermediate construction 100 for forming a femoral head resurfacing implant in accordance with an embodiment of the present disclosure. FIG. 3A shows a resurfacing head 110 and stem 120 of the intermediate construction 100 as well as a porous region 130 formed on an internal surface of the resurfacing head 110. As can be seen from FIG. 3A, the porous region 130 becomes progressively thinner as one nears a distal end 110*d* of the resurfacing head 110. FIG. 3B separately shows the substantially nonporous regions of the intermediate construction 100 (resurfacing head 110, stem 120 and capping structure 125) of FIG. 3A. FIG. 3C separately shows the porous region 130 that is formed at the internal surface of the resurfacing head 110 of FIG. 3A.

As best seen from FIG. 3B, in various embodiments, the present disclosure provides the intermediate construction 100 with capping structures 125 which can, for example, include holes, pockets, voids, angled planes and/or elevated walls, among other features, that serve several purposes throughout the manufacturing process. For example, a capping structure 125 may be provided to enhance the strength of intermediate construction 100 during manufacture, for instance, resisting warpage at the rim of the intermediate construction 100 that may otherwise be caused by thermal stresses due to heat treatment during the manufacturing progress. In addition, a capping structure 125 may provide the ability to remove residual powder arising from the additive manufacturing process that would otherwise be trapped within the intermediate construction 100 (see the generally triangular apertures 125*a* in FIG. 3B). A capping structure 125 may also provide work holding points for computer numerical control (CNC) machining, and may limit the number of support structures (e.g., the gussets as discussed below), if any, that are included within the intermediate construction 100. In some embodiments, a capping structure 125 may provide a way to process the intermediate construction in post-additive thermal treatment without introducing oxygen to the porous region 130. To form the final resurfacing implant structure, the capping structure 125 can be removed from the intermediate construction (e.g., by a suitable machining process).

As seen from FIG. 3C, the intermediate construction 100 includes a porous region 130 which includes various support structures, specifically, a plurality of porous gussets 130*g* in the embodiment shown, which enhance the strength of the intermediate construction 100 during manufacture, for example, in terms of buckling, shear yielding and/or warpage. As with the capping structure 125, all or a portion of the porous gussets 130*g* can be removed (e.g., by a suitable machining process) to form the final implant structure. An aperture 130*a* is shown in the porous region 130 which accommodates the stem 120 of the intermediate construction 100. The porous region 130 also provides a continuous region 130*r* in contact with the internal surface of the resurfacing head 110 in the embodiment shown.

Figure 3D:
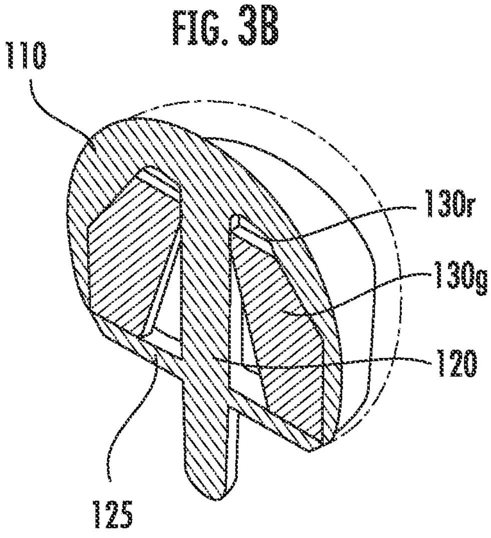
FIG. 3D is a longitudinal cross-section of the intermediate construction of FIG. 3A.
Figure 3E:
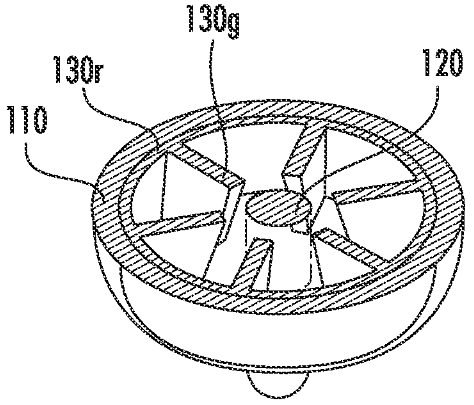
FIG. 3E is a transverse cross-section of the intermediate construction of FIG. 3A.

The longitudinal cross-section of FIG. 3D and the transverse cross-section of FIG. 3E show further details of the intermediate construction 100, including further details of the spatial relationships between the porous gussets 130*g* of the porous region 130 and the stem 120 and capping structure 125 of the intermediate construction 100, and the spatial relationships between the continuous region 130*r* of the porous region 130 and the internal surface of the resurfacing head 110.

Figure 4A:
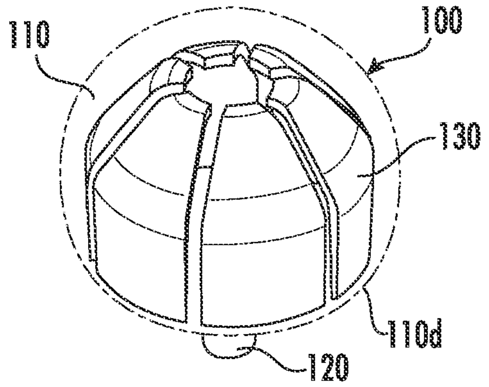
FIG. 4A is perspective view of another embodiment of an intermediate construction useful for forming a resurfacing implant in accordance with one or more features of the present disclosure.
Figure 4B:
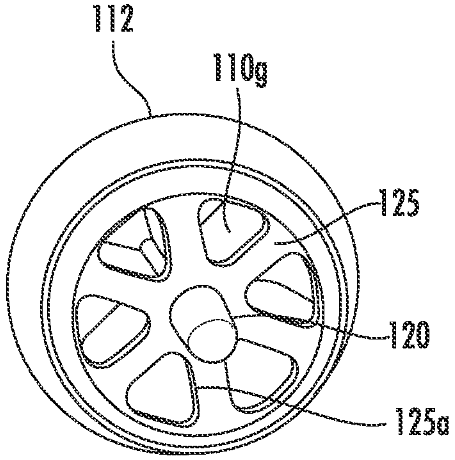
FIG. 4B is perspective view of substantially nonporous regions (e.g., resurfacing head, gussets, stem and cap) of the intermediate construction of FIG. 4A.
Figure 4C:
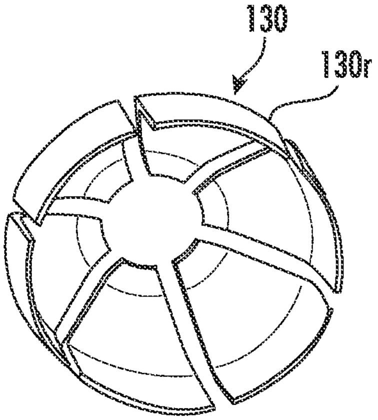
FIG. 4C is perspective view of porous regions of the intermediate construction of FIG. 4A.

Another embodiment of an intermediate construction 100 for forming a femoral head resurfacing implant in accordance with the present disclosure is shown in FIGS. 4A-4E. With reference now to FIG. 4A, an intermediate construction 100 is illustrated in a partially transparent perspective view and shows a resurfacing head 110 and stem 120 of the intermediate construction 100 as well as a porous region 130 formed on the internal surface of the resurfacing head 110. As can be seen from FIG. 4A, the porous region 130 become progressively thinner as one approaches a distal end 110*d* of the resurfacing head 110. FIG. 4B separately shows substantially nonporous regions of the intermediate construction 100 (resurfacing head 110, gussets 110*g*, stem 120 and capping structure 125) of FIG. 4A. FIG. 4C separately shows the porous regions 130 that are formed at the internal surface of the resurfacing head 110 of FIG. 4A.

As with FIGS. 3A-3E above, the intermediate construction 100 of FIGS. 4A-4E includes a capping structure 125 which includes a plurality of generally triangular apertures 125*a*. Unlike FIGS. 3A-3E, however, the intermediate construction 100 of FIGS. 4A-4E further includes a plurality of substantially nonporous internal support structures, specifically a plurality of substantially nonporous gussets 110*g* in the embodiment shown, which extend inward from the internal surface of the resurfacing head 110 to the stem 120 and, like the porous gussets 130*g* described above, provide the intermediate construction 100 with enhanced strength. Along with the capping structure 125, all or a portion of the gussets 110*g* can be removed (e.g., by a suitable machining process) to form the final resurfacing implant structure. Moreover, as seen from FIG. 4C, the porous region 130 is in the form of multiple discontinuous porous regions 130*r* in contact with the internal surface of the resurfacing head 110, with no porous gussets provided in the embodiment shown.

Figure 4D:
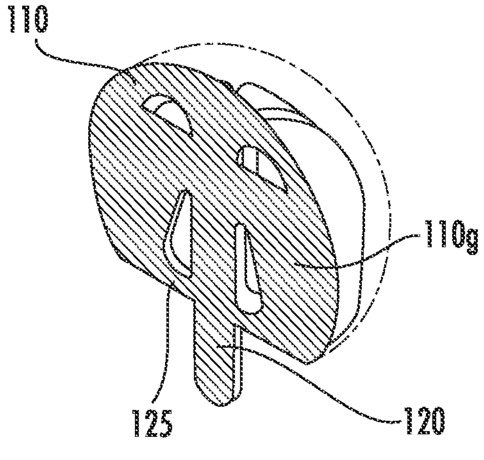
FIG. 4D is a longitudinal cross-section of the intermediate construction of FIG. 4A.
Figure 4E:
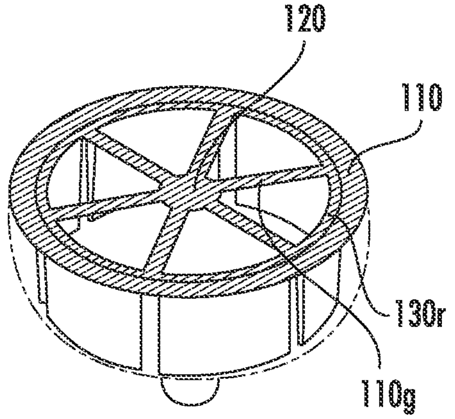
FIG. 4E is a transverse cross-section of the intermediate construction of FIG. 4A.

The longitudinal cross-section of FIG. 4D and the transverse cross-section of FIG. 4E show further details of the intermediate construction 100, including further details of the spatial relationships between the multiple discontinuous porous regions 130*r* and the internal surface of the resurfacing head 110 and the spatial relationships between the stem 120, the capping structure 125, substantially nonporous gussets 110*g* and the resurfacing head 110. In this regard, it is noted that, in the cross-section of FIG. 4D, the resurfacing head 110, stem 120, capping structure 125 and gussets 110*g* form a single continuous substantially nonporous cross-section.

Figure 5A:
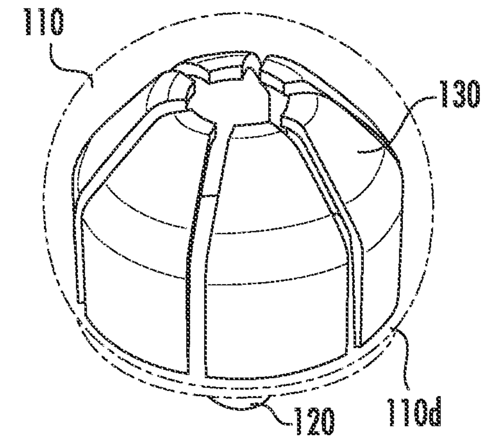
FIG. 5A is perspective view of another embodiment of an intermediate construction useful for forming a resurfacing implant in accordance with one or more features of the present disclosure.
Figure 5B:
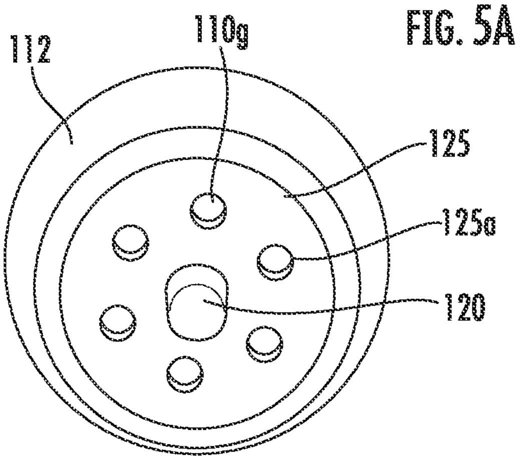
FIG. 5B is perspective view of substantially nonporous regions (e.g., resurfacing head, gussets, stem and cap) of the intermediate construction of FIG. 5A.
Figure 5C:
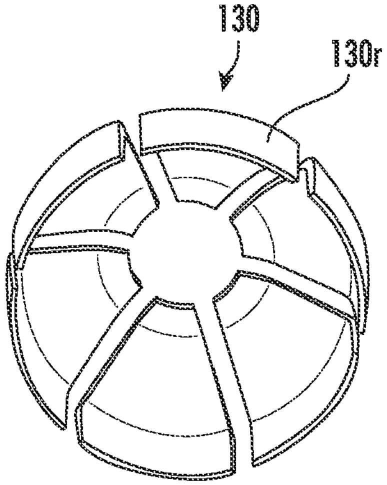
FIG. 5C is perspective view of porous regions of the intermediate construction of FIG. 5A.

Another embodiment of an intermediate construction 100 for a femoral head resurfacing implant in accordance with the present disclosure is shown in FIGS. 5A-5C. With reference now to FIG. 5A, a femoral head intermediate construction 100 is illustrated in a partially transparent perspective view and shows a resurfacing head 110 and stem 120 of the intermediate construction 100 as well as porous regions 130 formed at the internal surface of the resurfacing head 110. As can be seen from FIG. 5A, the porous regions 130 become progressively thinner as one approaches a distal end 110*d* of the resurfacing head 110. FIG. 5B separately shows the substantially nonporous regions of the intermediate construction 100 (resurfacing head 110, gussets 110*g*, stem 120 and capping structure 125). FIG. 5C separately shows the porous regions 130 that are formed at the internal surface of the resurfacing head 110.

As with intermediate construction 100 of FIGS. 4A-4E above, the intermediate construction 100 of FIGS. 5A-5C includes a capping structure 125 which includes a plurality of apertures, in this case a plurality of generally circular apertures 125*a*. Also, like FIGS. 4A-4E, the intermediate construction 100 of FIGS. 5A-5C includes a plurality of support structures, specifically a plurality of substantially nonporous gussets 110*g*, which extend inward from the internal surface of the resurfacing head 110 and enhance the strength of the femoral head intermediate construction 100. As with the capping structure 125, all or a portion of the gussets 110*g* can be removed (e.g., by a suitable machining process) to form the final resurfacing implant structure. Moreover, as seen from FIG. 5C, the porous region 130 is in the form of multiple discontinuous porous regions 130*r*, which are in contact with the internal surface of the resurfacing head 110.

Additively manufactured resurfacing implants and intermediate constructions in accordance with the present disclosure can be formed from a variety of materials. In various embodiments, the porous regions and the substantially nonporous regions of the resurfacing implants and intermediate constructions of the present disclosure may be formed from metallic materials selected from the group consisting of zirconium, zirconium alloys (e.g., Zr-2.5 Nb, among others), titanium, titanium alloys (e.g., Ti-6Al-4V or Ti-6AL-4V ELI, among others), tantalum, hafnium, niobium and any combination thereof, or cobalt-chromium alloys and stainless steel, among others. In various embodiments, the porous regions and the substantially nonporous regions are made of the same metallic material.

In some embodiments the substantially nonporous regions, the porous regions, or both may have an oxide, diffusion hardened or ceramic surface which may be formed after the implant has been additively manufactured from metal powders as described below. For example, in a particular embodiment, one or more porous regions and one or more substantially nonporous regions of a resurfacing implant or intermediate construction are additively manufactured from a zirconium alloy material. Subsequently, the resurfacing implant or intermediate construction is subjected to a heat treatment process in the presence of oxygen such that a ceramic zirconium oxide layer is formed on at least the external articulating surface of the resurfacing head to enhance wear resistance. Typically, the external articulating surface of the resurfacing head is polished to limit wear between the head and liner construct.

Further embodiments of the present disclosure pertain to methods for the fabrication of resurfacing implants and intermediate constructions like those described above. In various embodiments, the resurfacing implants or the intermediate constructions are formed by using additive manufacturing techniques. Additive manufacturing techniques include those known in the art such as solid free-form fabrication (SFF), selective laser sintering (SLS), direct metal fabrication (DMF), direct metal laser sintering (DMLS), electron beam melting (EBM), and selective laser melting (SLM), among others. Additive manufacturing methods allow for three-dimensional structures to be constructed one layer at a time from a powder which is solidified by irradiating a layer of the powder with an energy source such as a laser or an electron beam. The powder may be selectively melted in some regions, thereby forming substantially nonporous regions. In other regions, the lack of completely fused powder provides the porous regions. Such substantially nonporous regions and porous regions can be formed by the application of energy from the energy source, which may be directed in raster-scan fashion to selected portions of the powder layer to melt, fuse and/or sinter the powder. After forming a pattern in one powder layer, an additional layer of powder is dispensed, and the process is repeated until the desired structure is complete.

The desired structures can be formed directly from computer-controlled databases, which greatly reduces the time and expense required to fabricate the resurfacing implants or intermediate constructions. For example, a computer-aided system may be employed that has an energy source such as a laser or an electron beam to melt, fuse and/or sinter powder to build the structure one layer at a time according to a model selected in a database of the computer component of the system. In such additive fabrication systems, implants or intermediate constructions are formed by sequential delivery of material and/or energy to specified points in space to produce the implant or intermediate construction. More particularly, the resurfacing implants or intermediate constructions of the present disclosure can be produced in a layer-wise fashion from metallic powders that are dispensed one layer at a time, allowing for the direct manufacture of 3-D structures of high resolution and dimensional accuracy from a variety of materials.

In some embodiments, an initial powder layer may be placed onto a build plate. Thereafter, multiple layers of powder may be melted, fused and/or sintered due to application of energy from the energy source until the desired structure is complete. In some embodiments, the build plate may form a part of the resurfacing implant that is implanted into the patient. In some embodiments, the build plate may be removed from the intermediate construction, for example, using a suitable machining process.

Figure 6:
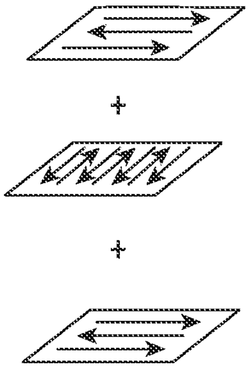
FIG. 6 is schematic illustration of an additive process in accordance with one or more features of the present disclosure.

In some embodiments, an alternating dual directional laser scan may be employed when building the resurfacing implant or intermediate construction as shown by arrows for three consecutive layers in FIG. 6. This approach enables an almost completely dense regions with very little porosity to be formed. Also, by building the resurfacing implant or intermediate construction normal to the build plate, without angles or bends, the strength of the resurfacing implant or intermediate construction is increased, as the effect of cooling normal to the melt pool assists in the formation of columnar grains without segregation. Finally, management of laser power during the additive manufacturing process enables a continuous surface to be formed by avoiding excessive gaps between columnar grains.

In some embodiments, the metallic powders that are used in the above and other additive processes may selected from the group consisting of zirconium, zirconium alloys (e.g., Zr-2.5 Nb, among others), titanium, titanium alloys (e.g., Ti-6Al-4V or Ti-6AL-4V ELI, among others), tantalum, hafnium, niobium and any combination thereof, or cobalt-chromium alloys and stainless steel, among others.

As previously noted, in some embodiments, the additively manufactured implant or intermediate construction may be subjected to a thermal treatment process at a selected temperature, atmospheric content and atmospheric pressure for a selected duration. Such a thermal treatment may increase the bond strength of the powder particles to one another. Such a thermal treatment may also be used to convert the exterior surface of the implant or intermediate construction into a ceramic like material.

In one specific embodiment of the present disclosure, a zirconium alloy powder, such as a Zr-2.5 Nb alloy powder, may be used to additively manufacture a resurfacing implant or intermediate construction as discussed elsewhere herein. Subsequently, the additively manufactured resurfacing implant or intermediate construction is subjected to thermal treatment at a temperature ranging from 600 to 715 degrees Celsius, in air or diffusion hardening species at a pressure ranging from atmospheric to $10^{-6}$ torr (vacuum), for a period ranging from 5 to 24 hours. The air oxidation and vacuum hardening steps could be carried out sequentially. Single or multiple thermal treatment cycles in this range of time, temperature and pressure can produce a ceramic surface layer of 3 to 8 μm thickness and oxygen rich diffusion hardened zone of 2 to 35 μm.

After thermal treatment, all or a portion of any capping structure or internal support structure(s) that is/are present, may be removed, for example, by a suitable machining process.

While the present disclosure refers to certain embodiments, numerous modifications, alterations, and changes to the described embodiments are possible without departing from the sphere and scope of the present disclosure, as defined in the appended claim(s). Accordingly, it is intended that the present disclosure not be limited to the described embodiments, but that it has the full scope defined by the language of the following claims, and equivalents thereof. The discussion of any embodiment is meant only to be explanatory and is not intended to suggest that the scope of the disclosure, including the claims, is limited to these embodiments. In other words, while illustrative embodiments of the disclosure have been described in detail herein, it is to be understood that the inventive concepts may be otherwise variously embodied and employed, and that the appended claims are intended to be construed to include such variations, except as limited by the prior art.

Directional terms such as top, bottom, superior, inferior, medial, lateral, anterior, posterior, proximal, distal, upper, lower, upward, downward, left, right, longitudinal, front, back, above, below, vertical, horizontal, radial, axial, clockwise, and counterclockwise) and the like may have been used herein. Such directional references are only used for identification purposes to aid the reader's understanding of the present disclosure. For example, the term "distal" may refer to the end farthest away from the medical professional/operator when introducing a device into a patient, while the term "proximal" may refer to the end closest to the medical professional when introducing a device into a patient. Such directional references do not necessarily create limitations, particularly as to the position, orientation, or use of this disclosure. As such, directional references should not be limited to specific coordinate orientations, distances, or sizes, but are used to describe relative positions referencing particular embodiments. Such terms are not generally limiting to the scope of the claims made herein. Any embodiment or feature of any section, portion, or any other component shown or particularly described in relation to various embodiments of similar sections, portions, or components herein may be interchangeably applied to any other similar embodiment or feature shown or described herein.

While the present disclosure refers to certain embodiments, numerous modifications, alterations, and changes to the described embodiments are possible without departing from the sphere and scope of the present disclosure, as defined in the appended claim(s). Accordingly, it is intended that the present disclosure not be limited to the described embodiments. Rather these embodiments should be considered as illustrative and not restrictive in character. All changes and modifications that come within the spirit of the invention are to be considered within the scope of the disclosure. The present disclosure should be given the full scope defined by the language of the following claims, and equivalents thereof. Unless otherwise defined, all technical terms used herein have the same meaning as commonly understood by one of ordinary skill in the art to which the disclosure belongs.

The foregoing description has broad application. The discussion of any embodiment is meant only to be explanatory and is not intended to suggest that the scope of the disclosure, including the claims, is limited to these embodiments. In other words, while illustrative embodiments of the disclosure have been described in detail herein, it is to be understood that the inventive concepts may be otherwise variously embodied and employed, and that the appended claims are intended to be construed to include such variations, except as limited by the prior art.

It should be understood that, as described herein, an "embodiment" (such as illustrated in the accompanying Figures) may refer to an illustrative representation of an environment or article or component in which a disclosed concept or feature may be provided or embodied, or to the representation of a manner in which just the concept or feature may be provided or embodied. However, such illustrated embodiments are to be understood as examples (unless otherwise stated), and other manners of embodying the described concepts or features, such as may be understood by one of ordinary skill in the art upon learning the concepts or features from the present disclosure, are within the scope of the disclosure. Furthermore, references to "one embodiment" of the present disclosure are not intended to be interpreted as excluding the existence of additional embodiments that also incorporate the recited features.

In addition, it will be appreciated that while the Figures may show one or more embodiments of concepts or features together in a single embodiment of an environment, article, or component incorporating such concepts or features, such concepts or features are to be understood (unless otherwise specified) as independent of and separate from one another and are shown together for the sake of convenience and without intent to limit to being present or used together. For instance, features illustrated or described as part of one embodiment can be used separately, or with another embodiment to yield a still further embodiment. Thus, it is intended that the present subject matter covers such modifications and variations as come within the scope of the appended claims and their equivalents.

As used herein, an element or step recited in the singular and proceeded with the word "a" or "an" should be understood as not excluding plural elements or steps, unless such exclusion is explicitly recited. It will be further understood that the terms "comprises" and/or "comprising," or "includes" and/or "including" when used herein, specify the presence of stated features, regions, steps, elements and/or components, but do not preclude the presence or addition of one or more other features, regions, integers, steps, operations, elements, components and/or groups thereof.

The phrases "at least one", "one or more", and "and/or", as used herein, are open-ended expressions that are both conjunctive and disjunctive in operation. The terms "a" (or "an"), "one or more" and "at least one" can be used interchangeably herein.

Connection references (e.g., engaged, attached, coupled, connected, and joined) are to be construed broadly and may include intermediate members between a collection of elements and relative to movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another. The drawings are for purposes of illustration only and the dimensions, positions, order and relative to sizes reflected in the drawings attached hereto may vary.

The foregoing discussion has been presented for purposes of illustration and description and is not intended to limit the disclosure to the form or forms disclosed herein. For example, various features of the disclosure are grouped together in one or more embodiments or configurations for the purpose of streamlining the disclosure. However, it should be understood that various features of the certain embodiments or configurations of the disclosure may be combined in alternate embodiments or configurations. Moreover, the following claims are hereby incorporated into this Detailed Description by this reference, with each claim standing on its own as a separate embodiment of the present disclosure.

The invention claimed is:

1. A method for fabricating a structure comprising the steps of:

forming a first region of the structure;

forming a plurality of porous support structures to define a second region of the structure directly attached to the first region;

forming removable support structures attached to either one or both of the first region or the second region of the structure; and forming a plate attached to the removable support structures such that the plate overlies the second region.

2. The method of claim 1, further comprising the step of:

removing the removable support structures to separate the plate from the structure.

3. The method of claim 1, further comprising the step of:

polishing at least part of the first region of the structure.

4. The method of claim 1, further comprising the step of:

applying a treatment to at least a part of the plate without applying the treatment to the second region.

5. The method of claim 1, wherein the structure is in the form of an orthopedic implant.

6. The method of claim 1, wherein the forming steps are performed by additive manufacturing.

7. The method of claim 1, wherein the first region is nonporous and the second region is porous.

8. The method of claim 1, wherein the plate forming step forms a plurality of apertures configured for powder removal.

9. The method of claim 1, further comprising treating at least a portion of the structure while the plate overlies the second region.

10. A method for fabricating a structure, comprising:
forming a first region of the structure;
forming a second region of the structure;
forming removable support structures attached to the structure;
forming a plate attached to the removable support structures, wherein the plate overlies the second region;
treating the structure while the plate is attached to the structure; and
separating the plate from the structure after the treating step.

11. The method of claim 10, further comprising the step of:
heat treating the structure, the heat treating step being performed before a polishing step.

12. The method of claim 10, further comprising the step of:
machining the structure, the machining step being performed before the separating step.

13. The method of claim 10, wherein the plate forming step forms a plurality of apertures.

14. The method of claim 13, further comprising the step of:
removing powder through the plurality of apertures in the plate.

* * * * *